(12) United States Patent
Singh

(10) Patent No.: US 11,741,204 B2
(45) Date of Patent: *Aug. 29, 2023

(54) INTELLIGENT REAL TIME RESOURCE INSTRUMENT ACTIVATION USING ELECTROENCEPHALOGRAM SIGNALS

(71) Applicant: BANK OF AMERICA CORPORATION, Charlotte, NC (US)

(72) Inventor: Shailendra Singh, Maharashtra (IN)

(73) Assignee: BANK OF AMERICA CORPORATION, Charlotte, NC (US)

( * ) Notice: Subject to any disclaimer, the term of this patent is extended or adjusted under 35 U.S.C. 154(b) by 292 days.

This patent is subject to a terminal disclaimer.

(21) Appl. No.: 16/921,132

(22) Filed: Jul. 6, 2020

(65) Prior Publication Data
US 2022/0004608 A1   Jan. 6, 2022

(51) Int. Cl.
G06F 21/32 (2013.01)
H04L 9/40 (2022.01)
H04L 9/32 (2006.01)
G06N 20/00 (2019.01)
A61B 5/117 (2016.01)
A61B 5/38 (2021.01)
A61B 5/378 (2021.01)
G06V 40/10 (2022.01)

(52) U.S. Cl.
CPC .............. *G06F 21/32* (2013.01); *A61B 5/117* (2013.01); *A61B 5/378* (2021.01); *A61B 5/38* (2021.01); *G06N 20/00* (2019.01); *G06V 40/10* (2022.01); *H04L 9/3236* (2013.01); *H04L 63/102* (2013.01); *G06V 40/15* (2022.01)

(58) Field of Classification Search
CPC ......... G06F 21/32; A61B 5/117; A61B 5/378; A61B 5/38; G06N 20/00; G06V 40/10; G06V 40/15; H04L 9/3236; H04L 63/102; H04L 63/0861
See application file for complete search history.

(56) References Cited

U.S. PATENT DOCUMENTS

| | | | |
|---|---|---|---|
| 6,898,299 B1 | 5/2005 | Brooks | |
| 7,325,724 B2 | 2/2008 | Bonalle et al. | |
| 8,327,151 B2 | 12/2012 | Awatsu et al. | |
| 8,635,105 B2 | 1/2014 | Pradeep et al. | |
| 8,655,428 B2 | 2/2014 | Pradeep et al. | |
| 9,083,532 B2 | 7/2015 | Leddy et al. | |
| 9,320,450 B2 | 4/2016 | Badower | |
| 10,127,366 B2 | 11/2018 | Kohli | |
| 10,127,367 B2 | 11/2018 | Cherry et al. | |
| 10,127,369 B2 | 11/2018 | Kaehler | |
| 10,169,560 B2 * | 1/2019 | Cudak | G06F 21/32 |

(Continued)

*Primary Examiner* — Amie C. Lin
(74) *Attorney, Agent, or Firm* — Moore & Van Allen PLLC; Nicholas C. Russell

(57) ABSTRACT

Embodiments of the present invention provide a system for secure communication of information that may be used to authorize communications or transfer of resources by use of an intelligent resource instrument with nano display. The provided systems, methods, and computer program products are designed to select and display viewable information, simultaneously record EEG readings for a user, and use this information to verify user identity. Upon verification of user identity, the intelligent resource instrument may be activated for use in a resource transfer.

12 Claims, 5 Drawing Sheets

(56) References Cited

U.S. PATENT DOCUMENTS

| | | | |
|---|---|---|---|
| 10,362,024 B2 | 7/2019 | Jakobsson et al. | |
| 10,373,143 B2 | 8/2019 | Todeschini | |
| 2006/0289657 A1 | 12/2006 | Rosenberg | |
| 2008/0110983 A1 | 5/2008 | Ashfield | |
| 2009/0063866 A1 | 3/2009 | Navratil et al. | |
| 2012/0108995 A1 | 5/2012 | Pradeep et al. | |
| 2013/0086389 A1 | 4/2013 | Suwald | |
| 2014/0020089 A1 | 1/2014 | Perini | |
| 2015/0206148 A1* | 7/2015 | Cherry | G06Q 20/341 |
| | | | 705/41 |
| 2016/0224773 A1 | 8/2016 | Ramaci | |
| 2016/0253651 A1 | 9/2016 | Park et al. | |
| 2016/0275760 A1 | 9/2016 | Block et al. | |
| 2016/0342782 A1* | 11/2016 | Mullins | G02B 27/0176 |
| 2017/0050459 A1 | 2/2017 | Tiguy et al. | |
| 2017/0053277 A1 | 2/2017 | Dutt et al. | |
| 2017/0364920 A1 | 12/2017 | Anand | |
| 2018/0047014 A1* | 2/2018 | Maus | H04L 63/0838 |
| 2018/0285540 A1 | 10/2018 | Chen et al. | |
| 2018/0300487 A1* | 10/2018 | Gupta | G06N 20/00 |
| 2018/0332036 A1 | 11/2018 | Mokhasi | |
| 2018/0342176 A1 | 11/2018 | Califorrniaa | |
| 2019/0125203 A1 | 5/2019 | Castinado et al. | |
| 2019/0131002 A1 | 5/2019 | Castinado et al. | |
| 2021/0157886 A1 | 5/2021 | Kang et al. | |
| 2021/0271948 A1 | 9/2021 | Lowe | |

* cited by examiner

INTELLIGENT REAL TIME RESOURCE INSTRUMENT ACTIVATION USING ELECTROENCEPHALOGRAM SIGNALS

FIELD OF THE INVENTION

The present invention generally relates to resource instrument activation via the use of electroencephalogram (EEG) technologies for intelligent authorization and validation.

BACKGROUND

The transmission of resources can occur quickly and securely through the use of modern resource transfer mechanisms. While the simplicity of transferring information via a personalized resource transfer card can be convenient, resource security concerns may arise. As such, additional security measures, including the use of secure dynamic authorization credentials, are desired to protect the integrity of sensitive resources in resource transfer interactions. There is a need for enhanced dynamic authorization of resource instruments that is seamless and has a high degree of integrity in terms of authorization threshold for identity verification.

BRIEF SUMMARY

The following presents a summary of certain embodiments of the invention. This summary is not intended to identify key or critical elements of all embodiments nor delineate the scope of any or all embodiments. Its sole purpose is to present certain concepts and elements of one or more embodiments in a summary form as a prelude to the more detailed description that follows.

Electroencephalography (EEG) is a monitoring method to record electrical activity of the brain, and is a non-invasive approaches to brain computer interfacing, mainly due to its fine temporal resolution, ease of use, and portability. While EEG monitoring devices are typically utilized via multiple electrode contact points on a user's head, it is contemplated and anticipated in the present invention that EEG devices will continue to be increasingly highly portable, such as a wearable device that may utilize a low power wireless connection and dry electrodes, or a portable auxiliary component of a mobile wearable device. In some embodiments, the invention utilizes EEG readings to analyze and store unique user biometric patterns and attributes. In this way, the invention interconnects with a network for real-time data transfer from user devices, intelligent resource instruments, third party systems, and other connected devices to receive, analyze, and react to EEG data from an EEG reader. As such, upon receiving and analyzing unique user-specific EEG data, the system may form and activate a user specific EEG configuration and react by sending control signals to user devices for management of the user's experience, which pay include authorized activation of an intelligent resource instrument. In some embodiments, the intelligent resource instrument itself may contain a display element that acts as an activation mechanism for the production of EEG response signals from the user. By measuring, storing, and comparing EEG readings in correlation with specific activation signals, the system is able to authorize and validate user identity. Upon authorization and validation, the intelligence resource instrument may be authorized for use in transferring resources during a resource transaction.

Embodiments of the present invention address the above needs and/or achieve other advantages by providing apparatuses (e.g., a system, computer program product and/or other devices) and methods for dynamic and secure contactless distribution of resources. The system embodiments may comprise one or more memory devices having computer readable program code stored thereon, a communication device, and one or more processing devices operatively coupled to the one or more memory devices, wherein the one or more processing devices are configured to execute the computer readable program code to carry out the invention. In computer program product embodiments of the invention, the computer program product comprises at least one non-transitory computer readable medium comprising computer readable instructions for carrying out the invention. Computer implemented method embodiments of the invention may comprise providing a computing system comprising a computer processing device and a non-transitory computer readable medium, where the computer readable medium comprises configured computer program instruction code, such that when said instruction code is operated by said computer processing device, said computer processing device performs certain operations to carry out the invention.

For sample, illustrative purposes, system environments will be summarized. The system may generally comprise a system for intelligent resource instrument activation, the system comprising: a memory device; and a processing device operatively coupled to the memory device, wherein the processing device is configured to execute computer-readable program code to: receive a request from a user to initiate a resource action; in response to the request, transmit instructions to an resource instrument to emit an activation stimulus; record EEG readings for the user during a duration of the activation stimulus via an EEG wearable device; extract one or more patterns from the EEG readings and compare the one or more patterns to stored user data; determine a match between the one or more patterns and the stored user data; validate the identity of the user; and transmit an authorization signal to the resource instrument activating the resource instrument for use in the resource action.

In some embodiments, the activation stimulus further comprises a digital video or image displayed on a nano display of the resource instrument.

In some embodiments, the activation stimulus further comprises an auditory tone emitted from the resource instrument.

In some embodiments, the EEG readings are transmitted to the resource instrument and combined with data for the activation stimuli using a cryptographic hash algorithm.

In some embodiments, the intelligent resource instrument comprises a brain wave receptor for receiving the EEG readings.

In some embodiments, the invention further comprises using a machine learning engine to determine a match between the one or more patterns and the stored user data.

In some embodiments, the EEG readings are recorded using a portable wearable device.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
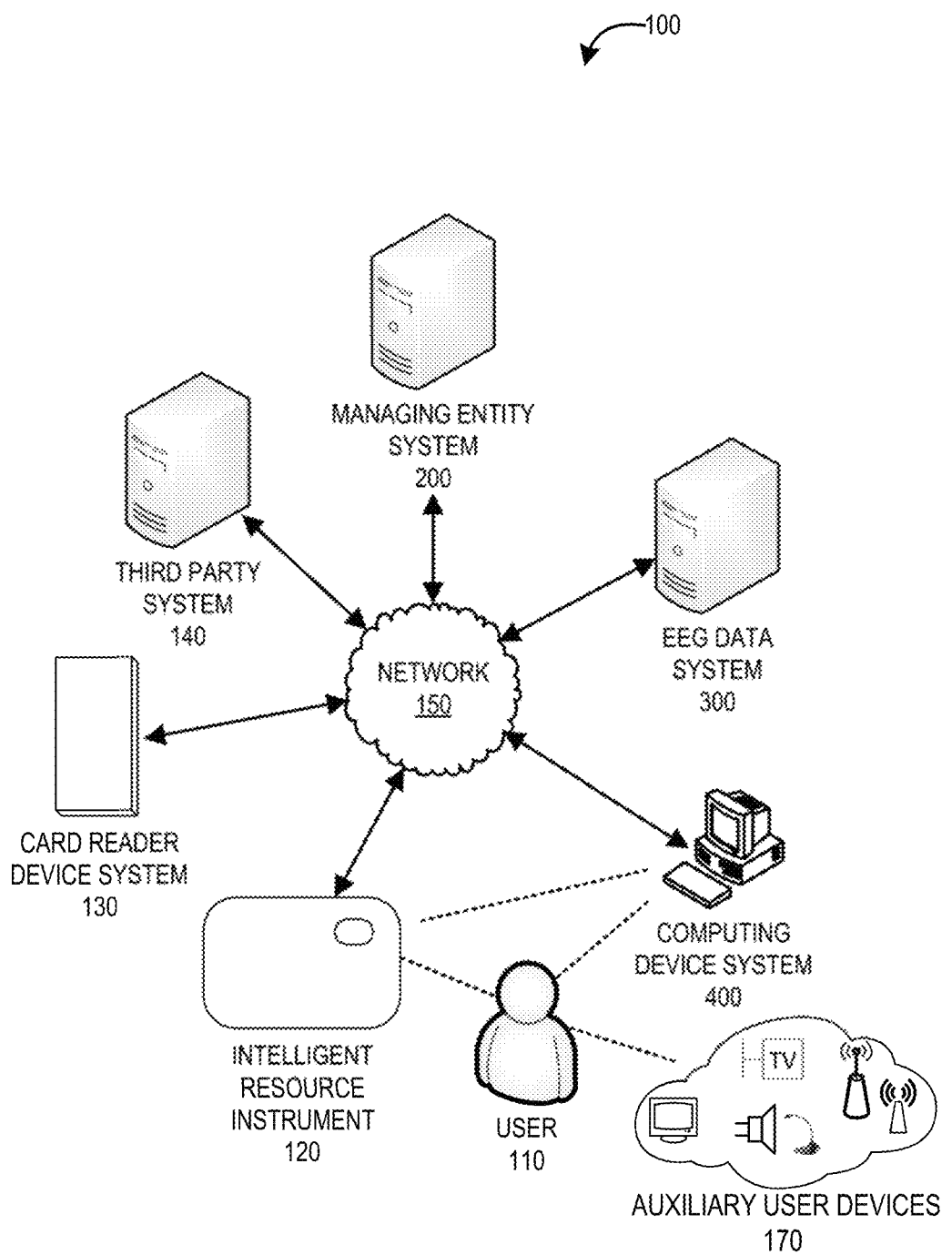
Figure 2:
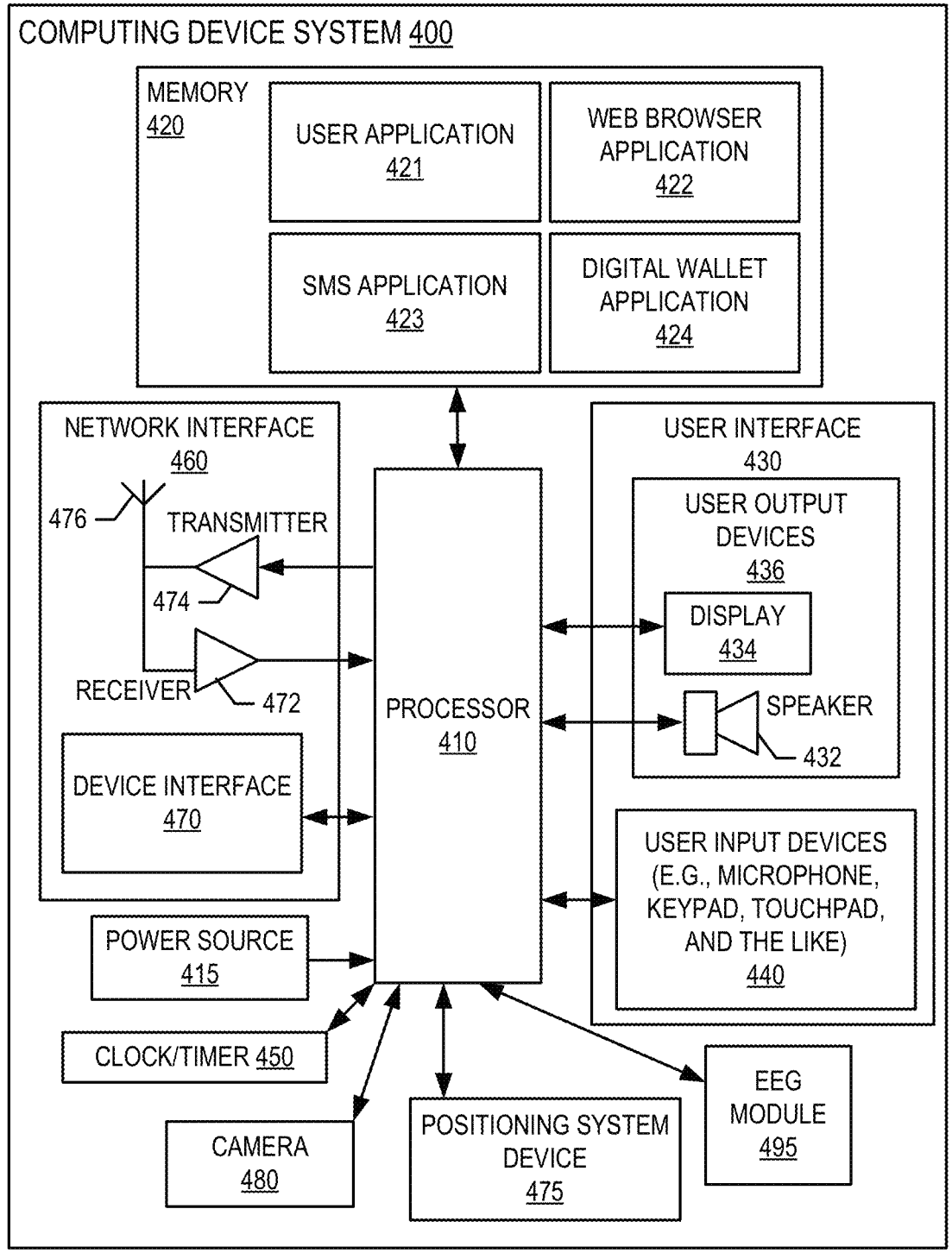
Figure 3:
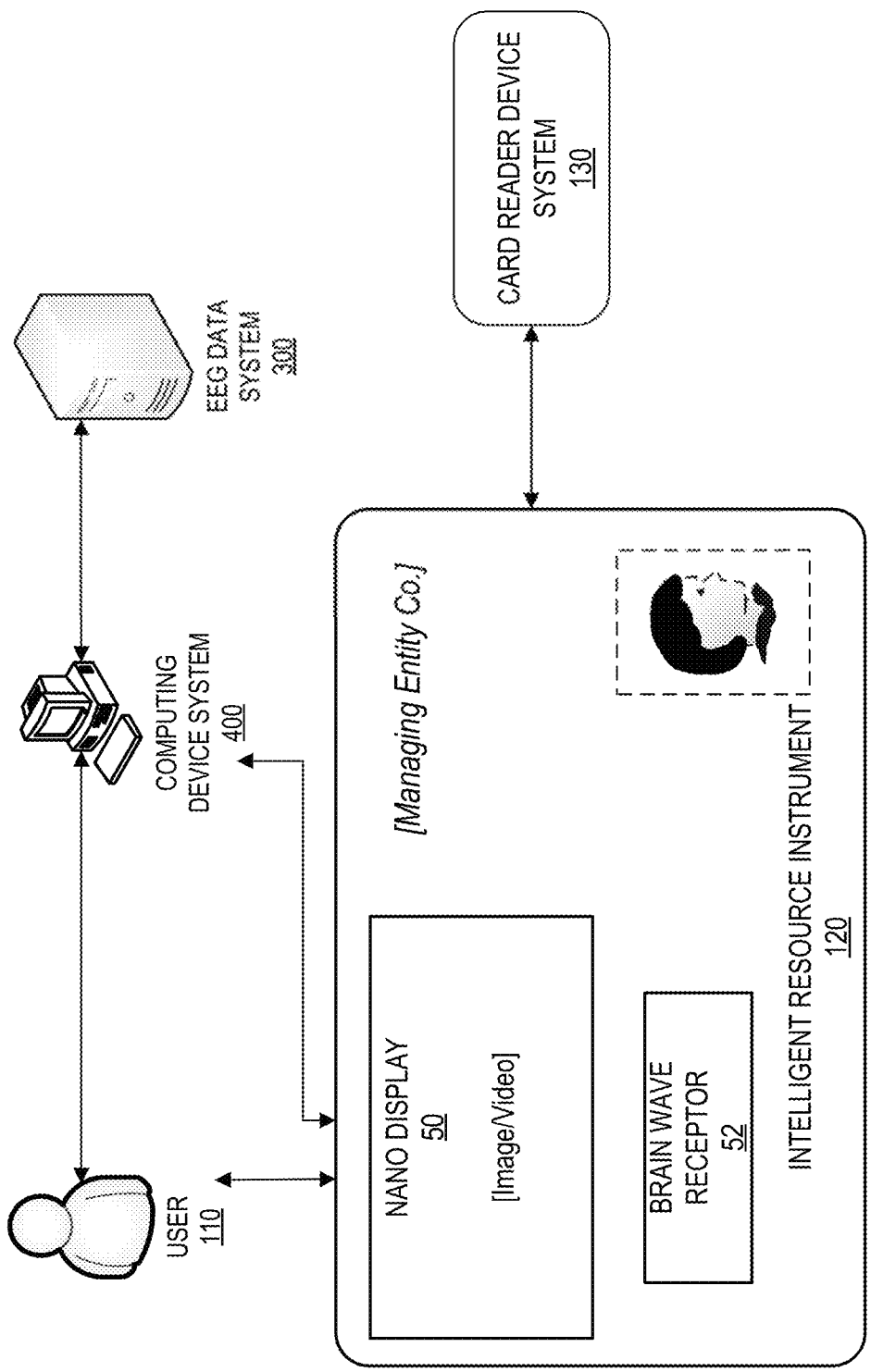
Figure 4:
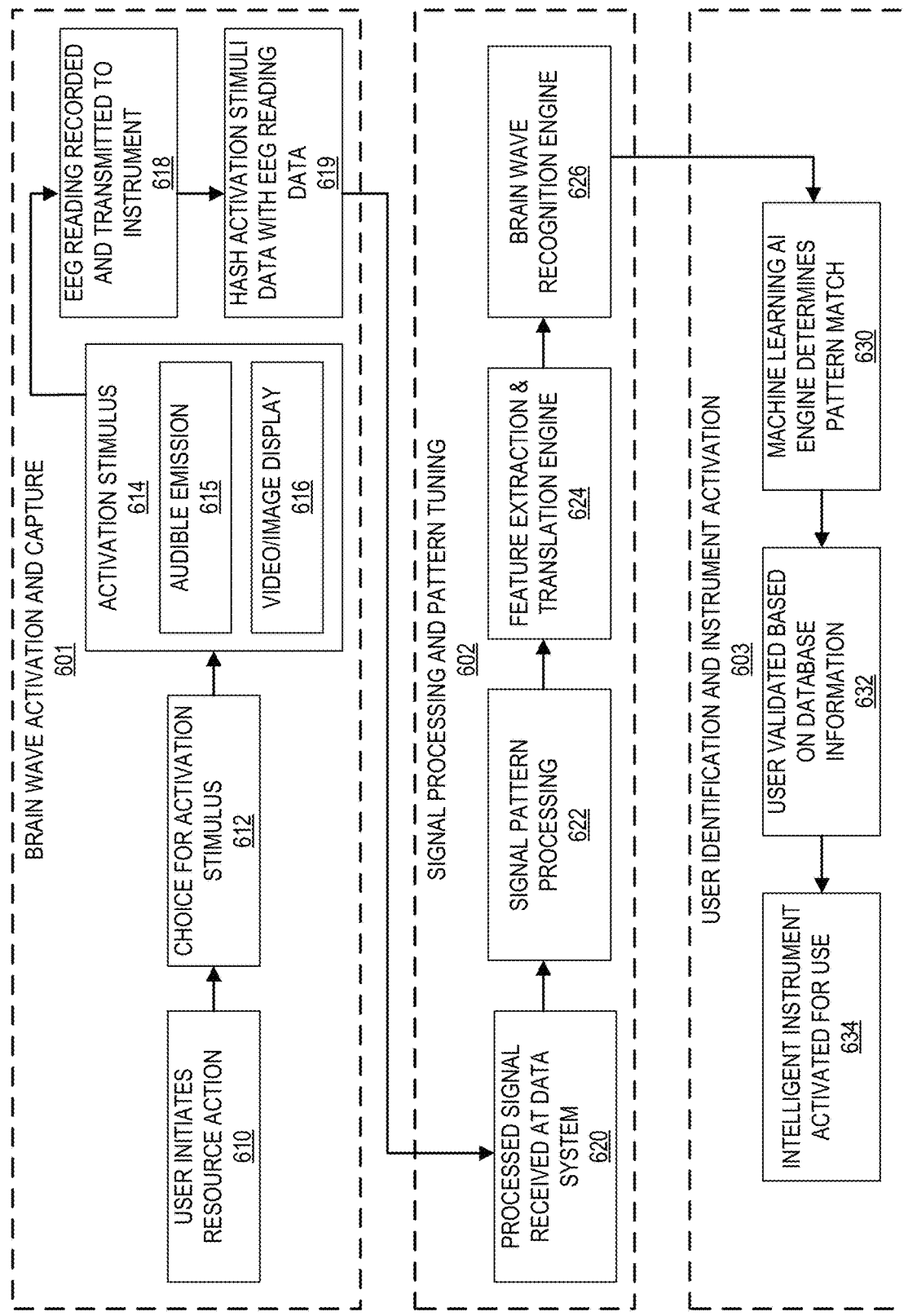
Figure 5:
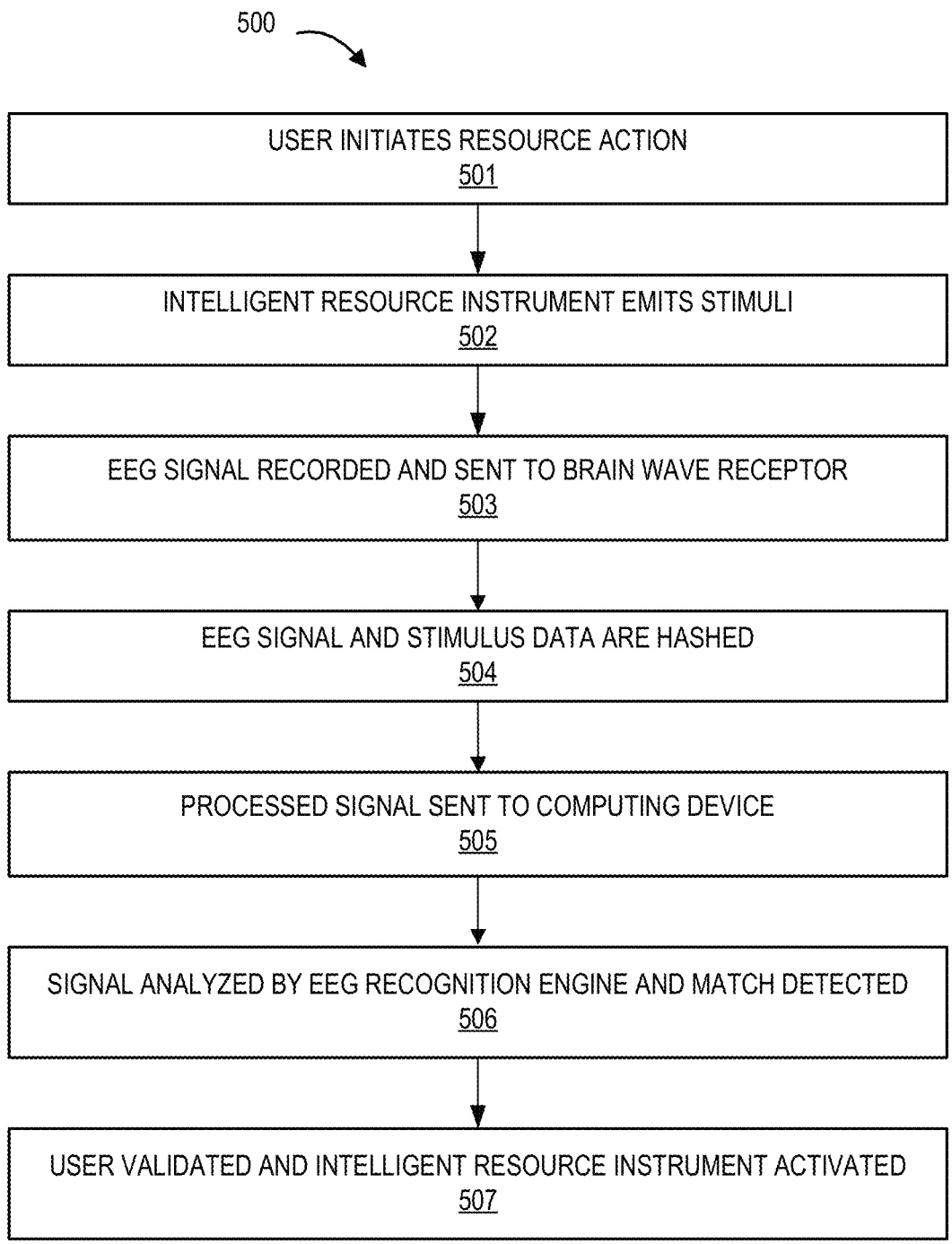

Having thus described embodiments of the invention in general terms, reference will now be made the accompanying drawings, wherein:

FIG. 1 provides a block diagram illustrating a system environment for intelligent resource instrument activation, in accordance with an embodiment of the invention;

FIG. 2 provides a block diagram illustrating the computing device system of FIG. 1, in accordance with an embodiment of the invention;

FIG. 3 provides a block diagram to illustrate the interface between intelligent resource instrument and instrument reader device system, in accordance with embodiments of the invention;

FIG. 4 provides a process flow diagram to illustrate the technical process for EEG reading analysis and user verification, in accordance with embodiments of the invention; and FIG. 5 provides a flowchart illustrating a process for resource transfer initiation using the intelligent resource instrument, in accordance with an embodiment of the invention.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on." Like numbers refer to like elements throughout.

As used herein, the term "resource action" may refer to the transfer of resources between one or more accounts, such as during the course of a purchase, sale, or the like. A "resource instrument" may refer to any instrument that can be utilized to facilitate the transfer of resources (e.g., credit card, debit card, gift card, loyalty card, check, or the like).

FIG. 1 provides a block diagram illustrating a system environment 100 for intelligent resource instrument activation, in accordance with an embodiment of the invention. As illustrated in FIG. 1, the environment 100 includes a managing entity system 200, a EEG data system 300, one or more computing device systems 400, an intelligent resource instrument 120 (e.g., a physical card with embedded display, brain wave receptor, or the like), one or more card reader device systems 130, and one or more third party systems 140. One or more users 110 may be included in the system environment 100. Also shown are one or more auxiliary user devices 170, which may be used by the user 110 and operatively connected to one or more of the other devices or systems shown in FIG. 1. In some embodiments, the user(s) 110 of the system environment 100 may be customers of a managing entity that controls or otherwise owns the managing entity system 200 and may, in some embodiments, comprise a financial institution.

The managing entity system 200, the EEG data system 300, the one or more computing device systems 400, the intelligent resource instrument 120, the card reader device system 130, and/or the third party system 140 may be in network communication across the system environment 100 through the network 150. The network 150 may include a local area network (LAN), a wide area network (WAN), and/or a global area network (GAN). The network 150 may provide for wireline, wireless, or a combination of wireline and wireless communication between devices in the network. In one embodiment, the network 150 includes the Internet. In some embodiments, the intelligent resource instrument 120 may be in connection with the network 150 only when the intelligent resource instrument 120 is within an interaction distance of the card reader device system 130, the third party system 140, or the computing device system 400, where the NFC interaction distance is a distance between the intelligent resource instrument 120 and reader device at which communication of information stored in the intelligent resource instrument 120 can occur.

The managing entity system 200 may be a system owned or otherwise controlled by a managing entity to perform one or more process steps described herein. In some embodiments, the managing entity is a financial institution. In general, the managing entity system 200 is configured to communicate information or instructions with the EEG data system 300, the one or more computing device systems 400, and/or the third party system 140 across the network 150. For example, the managing entity system 200 may maintain configuration data for the user 110 and therefore may receive a resource request associated with the user 110 (e.g., via a third party system 140 comprising a merchant system), compare received information to an internal database of a user configuration associated with the user 110, and transmit authentication or other approval information to the EEG data system 300, the card reader device system 130, the third party system 140, the computing device system 400, or the like. The managing entity system 200 may be configured to perform (or instruct other systems to perform) one or more other process steps described herein.

The EEG data system 300 may be a system owned or controlled by the managing entity and/or a third party that specializes in transactions involving intelligent resource instruments, dynamic card verification value systems, user authentication systems, transaction rule systems, and the like. In some embodiments, at least a portion of the EEG data system 300 may be controlled by or otherwise be a component of the managing entity system 200. In general, the EEG data system 300 is configured to communicate information or instructions with the managing entity system 200, the one or more computing device systems 400, the intelligent resource instrument 120, the card reader device system 130, and/or the third party system 140 across the network 150.

For example, the EEG data system 300 may receive dynamic data values from the third party system 140, the managing entity system 200, the computing device system 400, the card reader device system 130, auxiliary user devices 170, or the intelligent resource instrument 120 (e.g., indirectly, via another system). The EEG data system 300 may then compare received dynamic data values to an expected dynamic data value stored in a user configuration associated with the user to determine whether the dynamic data value matches the expected dynamic data value and automatically cause the computing device system 400 of the user 110 to populate a digital wallet application, activate the intelligent resource instrument 120. The EEG data system 300 may be configured to perform (or instruct other systems to perform) one or more other process steps described herein.

The computing device system 400 may be a system owned or controlled by the managing entity, the user 110, and/or a third party that specializes in providing computers, mobile devices, or other computing devices that are configured to securely store and maintain user resource account or configuration information and/or initiate resource transfer requests. The computing device system 400 may, in some embodiments, include a card reader, writer, or other module configured to interact with intelligent resource instruments, such as resource payment cards.

In general, the computing device system 400 is configured to communicate information or instructions with the managing entity system 200, the EEG data system 300, the intelligent resource instrument 120, the card reader device system 130, and/or the third party system 140 across the network 150. For example, the computing device system 400 may detect an interaction with the intelligent resource instrument 120, extract resource information from the intelligent resource instrument 120, including a dynamic data values, transmit the dynamic data value to the managing entity system 200 and/or the EEG data system 300, and receive a confirmation that the transmitted dynamic data value matches an expected dynamic data value for the user 110. Of course, the computing device system 400 may be configured to perform (or instruct other systems to perform) one or more other process steps described herein.

The intelligent resource instrument 120 may comprise any card or other physical device that includes a nano-display, or the like that is configured to store information, data, codes, or the like and display dynamic authorization information, activation signal information, or other information readable by the card reader device system 130, user 110, or computing device system 400. In some embodiments, the intelligent resource instrument 120 may be a physical card (e.g., a credit card, a debit card, a gift card, or the like). The intelligent resource instrument 120 may also be embedded within or otherwise be a component of another physical element including, but not limited to, a check, a receipt, a bill, a financial statement, an physical letter comprising an offer for a financial account, or the like.

In some embodiments, the intelligent resource instrument 120 is a component of the computing device system 400 (e.g., a nano-display embedded in or connected to a mobile phone, a smart watch, an Internet of things device, or the like). While a single intelligent resource instrument 120 is illustrated in FIG. 1, it should be known that multiple intelligent resource instruments 120 may be present in the system environment 100, and different intelligent resource instruments 120 may be utilized to perform one or more of the process steps described herein.

In some embodiments, the intelligent resource instrument 120 is in direct communication with, or is otherwise manipulated by a dynamic resource element (e.g., a dynamic card verification value, a dynamic card verification code, a digital dynamic card verification value, a time based number, a card-unique key, or the like). For example, in embodiments where the intelligent resource instrument 120 is stored on a physical card, the same physical card may additionally include a digital dynamic card verification value component that automatically, or in response to a user depressing a button on the card, causes the intelligent resource instrument 120 to transmit a dynamic resource value or dynamic data value to any card reader device system 130 or user 110. The dynamic resource value may comprise a multi-character code that is based on a specific algorithm associated with a user configuration of the user 110 that is associated with the intelligent resource instrument (and the physical card), such that the dynamic resource value at any given time will match an expected dynamic resource value that can be determined based on the specific algorithm. The dynamic resource value may, in some embodiments, be an ordered display of colorized blocks that indicate a certain authorization code and encryption type. In still other embodiments, the dynamic resource value may be displayed as an image or video that dynamically changes based on a user interaction, time interval, or the like.

The intelligent resource instrument 120 may be issued by the managing entity system 200, the EEG data system 300, or a third party system 140, and/or, in some embodiments, may be manipulated (e.g., data may be written onto the intelligent resource instrument 120) by the computing device system 400 associated with the user 110.

Information stored in the intelligent resource instrument 120 may comprise, but is not limited to, credit card information (e.g., card number information, user configuration information, billing information, and the like), debit card information, account information for the associated user 110, user configuration information associated with the user (e.g., shipping address, name, other accounts of the user 110, geographic region of the user 110, transaction rules established by or for the user 110, or the like), shipping information, authentication preference information, resource amount threshold information, approved transaction type information (e.g., approved merchants, approved product or service types, or the like), prohibited transaction type information (e.g., prohibited merchants, prohibited product or service types, or the like), an image associated with the user 110 (e.g., an image of the face of the user 110, a security image associated with the user 110, or the like), and transaction rules associated with the user 110 and/or an associated card or account of the user 110.

In some embodiments, this information stored in the intelligent resource instrument 120 may be stored in the form of standard codes that are readable by card reader devices (e.g., the card reader device system 130), nano-display reader modules, automated teller machines (ATMs), or the like. In some embodiments, at least some of the information stored in the intelligent resource instrument 120 comprises codes that can be extracted by card reader devices and then transmitted to the managing entity system 200 and/or the EEG data system 300 to prompt those systems to match the extracted codes to the associated information that can then be transmitted back to the card reader devices or associated devices or systems. For example, information that would otherwise require the transfer of a large amount of data (e.g., an image of the face of the user, a transaction rule, or the like) to efficiently effectuate the communication of that information from the intelligent resource instrument 120 to a card reader device system 130 (which may include a computing device system 400) may instead be communicated as a code which is communicated to the managing entity system 200, which in turn responds with the large amount of data.

The card reader device system 130 may comprise a network communication interface, a processing device, and one or more memory devices, where the processing devices are configured to perform certain actions with the memory devices and communicate these actions to the rest of the network 150 through the network communication interface.

The third party system 140 may be any system that interacts with the other systems and devices of the system environment 100 including, but not limited to, merchant systems, automated teller machine device systems, point of sale device systems, online merchant portal systems, regulatory agency systems, data storage systems, third party user authentication systems, third party credit card or debit card systems, transaction systems, and the like.

FIG. 2 provides a block diagram illustrating the computing device system of FIG. 1, in accordance with an embodiment of the invention. In one embodiment of the invention, the computing device system 400 is a mobile device. However, it should be understood that a mobile device or mobile telephone are merely illustrative of one type of computing device system 400 that may benefit from, employ, or otherwise be involved with embodiments of the present invention and, therefore, should not be taken to limit the scope of embodiments of the present invention. Other types of computing devices may include portable digital assistants (PDAs), pagers, mobile televisions, desktop computers, workstations, laptop computers, cameras, video recorders, audio/video player, radio, GPS devices, wearable devices, Internet-of-things devices, augmented reality devices, virtual reality devices, automated teller machine devices, electronic kiosk devices, or any combination of the aforementioned. In some embodiments, one or more of the functionalities or components of the computing device system 400 may be represented in whole or in part by one or more auxiliary devices 170.

Furthermore, it should be known that multiple computing device systems 400 may be owned by or accessed by the user 110 within the system environment 100 of FIG. 1, and these separate computing device systems 400 may be in network communication with each other and the other systems and devices of the system environment 100. For example, a first computing device system 400 may comprise a mobile phone of the user 110 that includes an NFC chip with resource data stored therein, and this mobile phone may be placed within an NFC interaction distance from an NFC reader device of a second computing device system 400 that comprises a personal computer of the user 110.

Some embodiments of the computing device system 400 include a processor 410 communicably coupled to such devices as a memory 420, user output devices 436, user input devices 440, a network interface 460, a power source 415, a clock or other timer 450, a camera 480, and a positioning system device 475. The processor 410, and other processors described herein, generally include circuitry for implementing communication and/or logic functions of the computing device system 400. For example, the processor 410 may include a digital signal processor device, a microprocessor device, and various analog to digital converters, digital to analog converters, and/or other support circuits. Control and signal processing functions of the computing device system 400 are allocated between these devices according to their respective capabilities. The processor 410 thus may also include the functionality to encode and interleave messages and data prior to modulation and transmission. The processor 410 can additionally include an internal data modem. Further, the processor 410 may include functionality to operate one or more software programs, which may be stored in the memory 420. For example, the processor 410 may be capable of operating a connectivity program, such as a web browser application 422. The web browser application 422 may then allow the computing device system 400 to transmit and receive web content, such as, for example, location-based content and/or other web page content, according to a Wireless Application Protocol (WAP), Hypertext Transfer Protocol (HTTP), and/or the like.

The processor 410 is configured to use the network interface 460 to communicate with one or more other devices on the network 150. In this regard, the network interface 460 includes an antenna 476 operatively coupled to a transmitter 474 and a receiver 472 (together a "transceiver"). The processor 410 is configured to provide signals to and receive signals from the transmitter 474 and receiver 472, respectively. The signals may include signaling information in accordance with the air interface standard of the applicable cellular system of a wireless network. In this regard, the computing device system 400 may be configured to operate with one or more air interface standards, communication protocols, modulation types, and access types. By way of illustration, the computing device system 400 may be configured to operate in accordance with any of a number of first, second, third, and/or fourth-generation communication protocols and/or the like. For example, the computing device system 400 may be configured to operate in accordance with second-generation (2G) wireless communication protocols IS-136 (time division multiple access (TDMA)), GSM (global system for mobile communication), and/or IS-95 (code division multiple access (CDMA)), or with third-generation (3G) wireless communication protocols, such as Universal Mobile Telecommunications System (UMTS), CDMA2000, wideband CDMA (WCDMA) and/or time division-synchronous CDMA (TD-SCDMA), with fourth-generation (4G) wireless communication protocols, with LTE protocols, with 4GPP protocols and/or the like. The computing device system 400 may also be configured to operate in accordance with non-cellular communication mechanisms, such as via a wireless local area network (WLAN) or other communication/data networks.

As described above, the computing device system 400 has a user interface that is, like other user interfaces described herein, made up of user output devices 436 and/or user input devices 440. The user output devices 436 include a display 430 (e.g., a liquid crystal display or the like) and a speaker 432 or other audio device, which are operatively coupled to the processor 410.

The user input devices 440, which allow the computing device system 400 to receive data from a user such as the user 110, may include any of a number of devices allowing the computing device system 400 to receive data from the user 110, such as a keypad, keyboard, touch-screen, touchpad, microphone, mouse, joystick, other pointer device, button, soft key, and/or other input device(s). The user interface may also include a camera 480, such as a digital camera.

The computing device system 400 may also include a positioning system device 475 that is configured to be used by a positioning system to determine a location of the computing device system 400. For example, the positioning system device 475 may include a GPS transceiver. In some embodiments, the positioning system device 475 is at least partially made up of the antenna 476, transmitter 474, and receiver 472 described above. For example, in one embodiment, triangulation of cellular signals may be used to identify the approximate or exact geographical location of the computing device system 400. In other embodiments, the positioning system device 475 includes a proximity sensor or transmitter, such as an RFID tag, that can sense or be sensed by devices known to be located proximate a merchant or other location to determine that the computing device system 400 is located proximate these known devices.

The computing device system 400 further includes a power source 415, such as a battery, for powering various circuits and other devices that are used to operate the computing device system 400. Embodiments of the computing device system 400 may also include a clock or other timer 450 configured to determine and, in some cases, communicate actual or relative time to the processor 410 or one or more other devices.

The computing device system 400 also includes a memory 420 operatively coupled to the processor 410. As used herein, memory includes any computer readable medium (as defined herein below) configured to store data, code, or other information. The memory 420 may include volatile memory, such as volatile Random Access Memory (RAM) including a cache area for the temporary storage of data. The memory 420 may also include non-volatile memory, which can be embedded and/or may be removable. The non-volatile memory can additionally or alternatively include an electrically erasable programmable read-only memory (EEPROM), flash memory or the like.

The memory 420 can store any of a number of applications which comprise computer-executable instructions/code executed by the processor 410 to implement the functions of the computing device system 400 and/or one or more of the process/method steps described herein. For example, the memory 420 may include such applications as a conventional web browser application 422, or a user application 421, a digital wallet application 424, (or any other application provided by the managing entity system 200). These applications also typically instructions to a graphical user interface (GUI) on the display 430 that allows the user 110 to interact with the computing device system 400, the managing entity system 200, and/or other devices or systems. In one embodiment of the invention, when the user 110 decides to enroll in a user application 421 program, the user 110 downloads, is assigned, or otherwise obtains the user application 421 from the managing entity system 200, or from a distinct application server (e.g., from the EEG data system 300). In other embodiments of the invention, the user 110 interacts with the managing entity system 200 or the EEG data system 300 via the web browser application 422 in addition to, or instead of, the user application 421. The same mechanisms may be put in place to install, store, or otherwise access the digital wallet application 424. The memory 420 of the computing device system 400 may comprise a Short Message Service (SMS) application 423 configured to send, receive, and store data, information, communications, alerts, and the like via a wireless telephone network.

The user application 421 may comprise an application stored in the memory 420 that is configured to control and/or communicate with a EEG module 495 of the mobile device system 400 to receive brain wave information (e.g., codes, signals, or the like) from EEG devices, intelligent resource instruments 120 (e.g., the intelligent resource instrument 120 described with respect to FIG. 1, or the like). The user application 421 may also be configured to communicate information received from the EEG module 495 to the digital wallet application 424, the web browser application 422, and/or the SMS application 423. In some embodiments, the user application 421 may be configured to receive instructions from a separate system (e.g., the managing entity system 200, the EEG data system 300, a separate computing device system 400, an card reader device system 130, and/or a third party system 140 like a merchant system) and cause one or more components of the computing device system 400 to perform one or more actions. For example, the user application 421 may be configured to receive instructions for erasing certain information from an intelligent resource instrument and writing new information on that instrument. The user application 421 may then cause the EEG module 495 to erase the certain information from an intelligent resource instrument that is within an interaction distance of the EEG module 495 and then write the new information onto the intelligent resource instrument.

The digital wallet application 424 of the computing device system 400 may comprise an application created by and/or managed by a financial institution that is configured to securely store financial information, resource account information, user configuration information, billing information, shipping information, authentication information, dynamic resource value information (e.g., dynamic card image or video information), or the like. The digital wallet application 424 may be configured to receive account or card information (e.g., credit card information) from that has been extracted from an intelligent resource instrument and automatically populate fields within the digital wallet application 424 with the extracted information. For example, the extracted information may be formatted such that the information type and the information field is known and by the digital wallet application 424 (e.g., based on position or coding within the extracted nano-display data) and can therefore be matched to an applicable field of the digital wallet application 424.

The digital wallet application 424 may additionally be configured to initiate or otherwise communicate information as part of a transaction request. For example, the user 110 may use the computing device system 400 to initiate a transaction by tapping or otherwise positioning the EEG module 495 of the computing device system 400 within an interaction distance from a point of sale device comprising an card reader device (e.g., the card reader device system 130). This interaction may prompt the digital wallet application 424 to provide transaction information (e.g., credit card information, user name, billing information, and/or the like), and the digital wallet application 424 may then transmit the transaction information to the point of sale device for the purpose of conducting and/or authenticating the requested transaction.

The memory 420 can also store any of a number of pieces of information, and data, used by the computing device system 400 and the applications and devices that make up the computing device system 400 or are in communication with the computing device system 400 to implement the functions of the computing device system 400 and/or the other systems described herein. For example, the memory 420 may include such data as transaction history data, positional data of the computing device system 400, and the like.

FIG. 3 provides a block diagram to illustrate the interface between intelligent resource instrument and instrument reader device system, in accordance with embodiments of the invention. As shown, the intelligent resource instrument 120 comprises a nano display 50 and a brain wave receptor 52, and is operatively connected to the card reader device system 130, computing device system 400, or one or more devices of the user 110 not shown (e.g., auxiliary devices 170, such as a standalone EEG measurement device, or the like). The intelligent resource instrument 120 is designed to display viewable activation stimuli via the nano display 50 which acts as an activation mechanism for the user 110. In this way, the computing device system 400 may interact with the intelligence resource instrument 120 and the user 110 in order to relay data about the display image or video, and the EEG readings collected from the user 110. The EEG data system may identify patterns unique to the user and the activation signal information shown to the user via the intelligent resource instrument in order to identify expected response information, as well as overall patterns unique to the user over a wider data set, which may be used to identify the user 110 or support a conclusion of identity verification.

It is understood that the data stream between the intelligent resource instrument and the computing device system 400 or other devices of the user 110 may be used to transmit data to the intelligent resource instrument 120, wherein EEG data may be combined with nano display data, hashed by the brain wave receptor 52, and returned as processed EEG verification information that the computing device system 400, or EEG data system 300 may then use to perform an authentication or validation. Hashes may be utilized in order to increase data security during transmission (e.g., in case of data intercept by an unauthorized third party, or the like). The hashes applied by the intelligent resource instrument may be pre-defined such that the EEG system 300 may decipher the hashed output using a pre-shared key, or the like. The hashes of the EEG reading data in combination with the stimuli data may be created before allowing the data to be transmitted to the computing device system 400 or EEG system 300. As such, in some embodiments of the invention the hashes may be compared against hash requirements (e.g., authorized hashes, unauthorized hashes, similarities or differences between hashes of the same system or other systems, or the like). When the hashes for the received data meet the hash requirements, the process may proceed.

In some embodiments, after validation or authentication occurs, the computing device system or EEG data system may then transmit an activation or authorization message to the intelligent resource instrument 120, thereby activating the intelligent resource instrument and allowing it to transmit resource transaction information to the card reader device system 130 (e.g., a point of sale device, or the like).

FIG. 4 provides a process flow diagram to illustrate the technical process for EEG reading analysis, in accordance with embodiments of the invention. As discussed previously, the use of EEG readings for authentication involves interaction between various system components in order to achieve the desired result. The EEG reading itself is a monitoring method to record electrical activity of the brain, and is a non-invasive approaches to brain computer interfacing, mainly due to its fine temporal resolution, ease of use, and portability. While EEG monitoring devices are typically utilized via multiple electrode contact points on a user's head, it is contemplated and anticipated in the present invention that EEG devices will continue to be increasingly highly portable, such as a wearable device that may utilize a low power wireless connection and dry electrodes, or a portable auxiliary component of a mobile wearable device.

In some embodiments, the invention utilizes EEG readings to analyze and store unique user biometric patterns and attributes. In this way, the invention interconnects with a network for real-time data transfer from user devices, intelligent resource instruments, third party systems, and other connected devices to receive, analyze, and react to EEG data from an EEG reader. As such, upon receiving and analyzing unique user-specific EEG data, the system may generate and store a user-specific EEG datastore. By sending control signals to user devices for management of the user's experience, which pay include authorized activation of an intelligent resource instrument, and activation stimuli thereon, the system may measure stimuli to determine if a biometric match can be made. By measuring, storing, and comparing EEG readings in correlation with specific activation stimuli, the system is able to authorize and validate user identity. Upon authorization and validation, the intelligence resource instrument may be authorized for use in transferring resources during a resource transaction.

The process for EEG analysis and validation of user identity verification generally involves the steps of brain wave activation and capture 601, signal processing and pattern tuning 602, and user identification and instrument verification 603, as shown in FIG. 4. The process begins at block 610, wherein the user initiates a resource action. In some embodiments, the user may initiate a resource action by via the auxiliary user device 170 or computing device system 400 (e.g., via a user application, web application, or the like), or alternatively via the intelligent resource instrument 120 itself (e.g., by pressing a button or other activation component on the intelligent resource instrument). In other embodiments, the resource action may be initiated via a third party, such as a merchant, or point of sale device. In some embodiments, the user may select a choice for activation stimulus, as shown in block 612. Again, it is understood that in various embodiments it is contemplated that the user may make this section via the auxiliary user device 170 or computing device system 400 (e.g., via a user application, web application, or the like), or alternatively via the intelligent resource instrument 120 itself. The activation stimulus 614 may take on a number of forms, including, but not limited to, an audible emission 615, or a video or image display 616.

As the activation stimulus 614 is enabled, an EEG reading is recorded and transmitted to the intelligent resource instrument, as shown in block 618. At the resource instrument, activation stimulus data and EEG reading data recorded for the user's response to the activation stimulus 618 are hashed to produce a processed signal which is transmitted for signal processing and pattern tuning at the EEG data system 300. In some embodiments, the hashing takes place on the intelligent resource instrument itself; however, in other embodiments, the computing system 400 or EEG data system may be configured to receive activation stimulus data from the intelligent resource instrument 120, also receive EEG readings separately from the EEG device, and perform the hashing of the two data feeds remotely. Hashes may be utilized in order to increase data security during transmission (e.g., in case of data intercept by an unauthorized third party, or the like). The hashes applied by the intelligent resource instrument may be pre-defined such that the EEG system 300 may decipher the hashed output using a pre-shared key, or the like. The hashes of the EEG reading data in combination with the stimuli data may be created before allowing the data to be transmitted to the computing device system 400 or EEG system 300. As such, in some embodiments of the invention the hashes may be compared against hash requirements (e.g., authorized hashes, unauthorized hashes, similarities or differences between hashes of the same system or other systems, or the like). When the hashes for the received data meet the hash requirements, the process may proceed.

In some embodiments, the processed signal is received at the EEG data system 300 from the intelligent resource instrument 120. At this stage, the EEG data system performs signal pattern processing, as shown in block 622, in order to process analog brain wave data into a digital signature. Next, the data is fed to a feature extraction and translation engine 624, wherein the various frequencies of the digital signature are identified and cataloged. The data is then sent to a brain wave recognition engine, as shown in block 626, wherein the cataloged frequencies of the digital signature may be further translated according to known patterns or observable phenomena in human brainwave activity (e.g., spectral analysis of EEG readings may be used to determine a P300 response to a stimulus, or the like).

Next, the processed signal and pattern identification data is analyzed using machine learning AI engine, as shown in block 630 in order to determine if there is a meaningful pattern or match between the results of the brain wave recognition engine 626 output and data previously stored for one or more users on the EEG data system 300. It is understood that discernable patterns may be detected on a per stimulus and user basis, wherein the same user is expected to have a unique response to the same stimulus in some way. In other embodiments, the machine learning model may compare EEG readings for a user in response to a number of different stimuli in order to discern a unique user-specific pattern between all of the user's responses. The artificial intelligence and neural network engines described herein generate enriched data that can then be analyzed by the EEG data system 300 to determine high-confidence matching of user identities and verification for the completion of one or more resource activities, such as the disbursement of resources. The system is configured to store a collection of data received by the system or third party systems 140 in order to provide a large amount of available training data that allows the system to develop a high level of adaptability to constantly changing environments or a wide array of various environmental conditions, stimuli, and user characteristics, as may be reflected in changes in a received data stream in real time during implementation of the system. Id the system is able to match the user's EEG readings with data for a known user who is authorized to use the intelligent resource instrument 120, the user may be validated based on database information, as shown in block 632. If the user is validated, the system may authorize the user to conduct the resource action, and transmit a signal to the intelligent resource instrument 120, a point of sale system, third party system 140, computing device system 400, or other system, with the purpose of activating the intelligent resource instrument 120 for use in one or more resource activities, as shown in block 634.

FIG. 5 provides a flowchart illustrating a process for resource transfer initiation, in accordance with an embodiment of the invention. As shown, the process begins at block 501, wherein the user initiates a resource action. In some embodiments, the user may initiate a resource action by pressing a physical button on the intelligent resource instrument 120, accessing a user application 421 on the computing device system 400, or the like, in order to prompt the intelligent resource instrument 120 to emit an activation stimulus, as shown in block 502. In some embodiments, the activation signal may be the display of certain programmable image or video data on the nano display 50 of the intelligent resource instrument 120. In other embodiments, the intelligent resource instrument 120 may contain a speaker, or may interface with the processor of the computing device system 400 in order to cause the speaker 432 to emit a specific sound, song frequency, or the like.

Simultaneously as the activation stimulus is emitted or activated on the intelligent resource instrument 120, EEG readings are recorded from the user 110 (e.g., by an auxiliary EEG device, the computing device system 400, or the like), and sent to the brain wave receptor 52 of the intelligent resource instrument 120. In some embodiments, the intelligent resource instrument may combine the specific activation signal information with the received EEG readings and hash the data in order to produce a processed signal which is sent to the computing device systems 400, as shown in block 505 (and as further discussed with regard to block 620 in FIG. 4).

The computing device system 400 may, in some embodiments, perform an authorization and validation of the user identify based on the processed signal. In other embodiments, the computing device system 400 may forward the processes signal to a machine learning AI engine or neural net of the EEG data system 300, in order to analyze the processed signal and determine a match for the user identity, as shown in block 506. At the conclusion of the process, if a match is detected, and the user is deemed as authorized to use the intelligent resource instrument 120, the user may be validated, and the intelligent resource instrument 120 may be activated via the transmission of an activation signal or message sent to the intelligent resource instrument 120, as shown in block 507.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, and the like), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s).

The computer-executable program code may also be loaded onto a computer or other programmable data processing apparatus to cause a series of operational steps to be performed on the computer or other programmable apparatus to produce a computer-implemented process such that the code portions which execute on the computer or other programmable apparatus provide steps for implementing the functions/acts specified in the flowchart and/or block diagram block(s). Alternatively, computer program implemented steps or acts may be combined with operator or human implemented steps or acts in order to carry out an embodiment of the invention.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

Embodiments of the present invention are described above with reference to flowcharts and/or block diagrams. It will be understood that steps of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

The invention claimed is:

1. A system for intelligent resource instrument activation, the system comprising:
   a memory device; and
   a processing device operatively coupled to the memory device, wherein the processing device is configured to execute computer-readable program code to:
   receive a request from a user to initiate a resource action;
   transmit instructions to an intelligent resource instrument to emit an activation stimulus from the intelligent resource instrument, wherein the intelligent resource instrument comprises a physical card, and wherein the activation stimulus emitted from the intelligent resource instrument comprises a digital video or image displayed on a nano display of the intelligent resource instrument;
   record electroencephalogram (EEG) readings via an EEG wearable device that is separated from the intelligent resource instrument for the user during a duration of the activation stimulus emitted from the intelligent resource instrument, wherein the EEG wearable device comprises a portable auxiliary component of a mobile wearable device, and wherein the EEG readings are transmitted to the intelligent resource instrument and combined with data for the activation stimulus using a cryptographic hash algorithm;
   extract one or more patterns from the EEG readings and compare the one or more patterns to stored user data;
   determine a match between the one or more patterns and the stored user data;
   validate an identity of the user; and
   transmit an authorization signal to the intelligent resource instrument activating the intelligent resource instrument for use in the resource action.

2. The system of claim 1, wherein the activation stimulus further comprises an auditory tone emitted from the intelligent resource instrument.

3. The system of claim 1, wherein the intelligent resource instrument comprises a brain wave receptor for receiving the EEG readings.

4. The system of claim 1, further comprising using a machine learning engine to determine a match between the one or more patterns and the stored user data.

5. A computer program product for intelligent resource instrument activation, the computer program product comprising a non-transitory computer-readable storage medium having computer-executable instructions which when executed by a processing device cause the processing device to:
   receive a request from a user to initiate a resource action;
   transmit instructions to an intelligent resource instrument to emit an activation stimulus from the intelligent resource instrument, wherein the intelligent resource instrument comprises a physical card, and wherein the activation stimulus emitted from the intelligent resource instrument comprises a digital video or image displayed on a nano display of the intelligent resource instrument;

record electroencephalogram (EEG) readings via an EEG wearable device that is separated from the intelligent resource instrument for the user during a duration of the activation stimulus emitted from the intelligent resource instrument, wherein the EEG wearable device comprises a portable auxiliary component of a mobile wearable device, and wherein the EEG readings are transmitted to the intelligent resource instrument and combined with data for the activation stimulus using a cryptographic hash algorithm;

extract one or more patterns from the EEG readings and compare the one or more patterns to stored user data;

determine a match between the one or more patterns and the stored user data;

validate an identity of the user; and transmit an authorization signal to the intelligent resource instrument activating the intelligent resource instrument for use in the resource action.

6. The computer program product of claim 5, wherein the activation stimulus further comprises an auditory tone emitted from the intelligent resource instrument.

7. The computer program product of claim 5, wherein the intelligent resource instrument comprises a brain wave receptor for receiving the EEG readings.

8. The computer program product of claim 5, further comprising using a machine learning engine to determine a match between the one or more patterns and the stored user data.

9. A computer implemented method for intelligent resource instrument activation, the computer implemented method comprising:

providing a computing system comprising a computer processing device and a non-transitory computer readable medium, where the non-transitory computer readable medium comprises configured computer program instruction code, such that when said instruction code is operated by said computer processing device, said computer processing device performs the following operations:

receiving a request from a user to initiate a resource action;

transmitting instructions to an intelligent resource instrument to emit an activation stimulus from the intelligent resource instrument, wherein the intelligent resource instrument comprises a physical card, and wherein the activation stimulus emitted from the intelligent resource instrument comprises a digital video or image displayed on a nano display of the intelligent resource instrument;

recording electroencephalogram (EEG) readings via an EEG wearable device that is separated from the intelligent resource instrument for the user during a duration of the activation stimulus emitted from the intelligent resource instrument, wherein the EEG wearable device comprises a portable auxiliary component of a mobile wearable device, and wherein the EEG readings are transmitted to the intelligent resource instrument and combined with data for the activation stimulus using a cryptographic hash algorithm;

extracting one or more patterns from the EEG readings and compare the one or more patterns to stored user data;

determining a match between the one or more patterns and the stored user data;

validating an identity of the user; and transmitting an authorization signal to the intelligent resource instrument activating the intelligent resource instrument for use in the resource action.

10. The computer implemented method of claim 9, wherein the activation stimulus further comprises an auditory tone emitted from the intelligent resource instrument.

11. The computer implemented method of claim 9, wherein the intelligent resource instrument comprises a brain wave receptor for receiving the EEG readings.

12. The computer implemented method of claim 9, further comprising using a machine learning engine to determine a match between the one or more patterns and the stored user data.

* * * * *